(12) United States Patent
Lulla et al.

(10) Patent No.: US 9,339,470 B2
(45) Date of Patent: May 17, 2016

(54) ANTI-RETROVIRAL COMBINATION

(75) Inventors: Amar Lulla, Maharashtra (IN); Geena Malhotra, Maharashtra (IN)

(73) Assignee: Cipla Limited, Mumbai (IN)

(*) Notice: Subject to any disclaimer, the term of this patent is extended or adjusted under 35 U.S.C. 154(b) by 691 days.

(21) Appl. No.: 12/810,301

(22) PCT Filed: Dec. 24, 2008

(86) PCT No.: PCT/GB2008/004291
§ 371 (c)(1),
(2), (4) Date: Sep. 16, 2010

(87) PCT Pub. No.: WO2009/081174
PCT Pub. Date: Jul. 2, 2009

(65) Prior Publication Data
US 2011/0008429 A1  Jan. 13, 2011

(30) Foreign Application Priority Data
Dec. 24, 2007  (IN) ......................... 2538/MUM/2007

(51) Int. Cl.
*A61K 9/24* (2006.01)
*A61K 31/34* (2006.01)
*A61K 31/427* (2006.01)
*A61K 9/20* (2006.01)

(52) U.S. Cl.
CPC ............... *A61K 9/209* (2013.01); *A61K 9/2095* (2013.01); *A61K 31/34* (2013.01); *A61K 31/427* (2013.01); *A61K 9/2077* (2013.01)

(58) Field of Classification Search
CPC ...... A61K 9/209; A61K 31/34; A61K 31/427
See application file for complete search history.

(56) References Cited

U.S. PATENT DOCUMENTS

| | | | |
|---|---|---|---|
| 5,141,867 A | 8/1992 | Ivanoff et al. | |
| 5,484,801 A | 1/1996 | Al-Razzak et al. | |
| 5,541,206 A | 7/1996 | Kempf et al. | |
| 5,674,882 A | 10/1997 | Kempf et al. | |
| 6,037,157 A | 3/2000 | Norbeck et al. | |
| 2005/0048112 A1* | 3/2005 | Breitenbach et al. | 424/464 |
| 2005/0084529 A1 | 4/2005 | Rosenberg et al. | |
| 2006/0135562 A1* | 6/2006 | Kraft et al. | 514/336 |
| 2007/0099902 A1* | 5/2007 | Dahl et al. | 514/221 |
| 2007/0208009 A1 | 9/2007 | Hoetelmans | |

FOREIGN PATENT DOCUMENTS

| | | |
|---|---|---|
| EP | 0674513 B1 | 9/1996 |
| JP | 2005511723 A | 4/2005 |
| JP | 2007504142 A | 3/2007 |
| RU | 2275361 C2 | 4/2006 |
| WO | 9007199 A1 | 6/1990 |
| WO | 9109872 A2 | 7/1991 |
| WO | 9222654 A1 | 12/1992 |
| WO | 9507696 A1 | 3/1995 |
| WO | 9701349 A1 | 1/1997 |
| WO | 9967254 A2 | 12/1999 |
| WO | 03049746 A2 | 6/2003 |
| WO | 2005039551 A2 | 5/2005 |
| WO | 2006055455 A1 | 5/2006 |
| WO | 2006091529 A2 | 8/2006 |
| WO | 2007068934 A2 | 6/2007 |
| WO | 2009081174 A2 | 7/2009 |
| WO | 2009081174 A3 | 7/2009 |

OTHER PUBLICATIONS

PREZISTA Package Insert (issued Jun. 2006 by Tibotec, Inc.).*
CAS Registry No. 206361-99-1 (Jun. 4, 1998).*
AbuBaker et al. "Copovidone" in Handbook of Pharmaceutical Excipients. Pharmaceutical Press (Fifth Edition) 2006; 201-203.*
Remington: The Science and Practice of Pharmacy. 21st Edition (2005) 891-893.*
Goicoechea, Miguel, and Brookie Best. "Efavirenz/emtricitabine/tenofovir disoproxil fumarate fixed-dose combination: first-line therapy for all?" Expert Opin. Pharmacother. (Feb. 2007) 8(3):371-382.*
Li, Shun Por, et al. "Evaluation of bilayer tablet machines—a case study." Drug development and industrial pharmacy 21.5 (1995): 571-590.*
Barin, F., et al., "Virus envelope protein of HTLV-III represents major target antigen for antibodies in AIDS patients," Science, May 31, 1985, vol. 228, pp. 1094-1096.
Barré-Sinoussi, J., et al., "Isolation of a t-lymphotropic retrovirus from a patient at risk for acquired immune deficiency syndrome (AIDS)," Science, May 20, 1983, vol. 220, pp. 868-871.
Clavel, François, et al., "Isolation of a new human retrovirus from West African patients with AIDS," Reports, Science, Jul. 18, 1986, vol. 233, pp. 343-346.
Foreign communication from the priority application—International Search Report and Written Opinion, PCT/GB2008/004291, Jul. 9, 2009, 8 pages.
Foreign communication from the priority application—International Preliminary Report on Patentability, PCT/GB2008/004291, Jun. 29, 2010, 6 pages.
Gallo, Robert C., et al., "Frequent detection and isolation of cytopathic retroviruses (HTLV-III) from patients with AIDS and at risk for AIDS," Science, May 4, 1984, vol. 224, pp. 500-503.
Guyader, Mireille, et al., "Genome organization and transactivation of the human immunodeficiency virus type 2," Nature, Apr. 16, 1987, vol. 326, pp. 662-669.
Hammarskjöld, Marie-Louise, et al., "The molecular biology of the human immunodeficiency virus," Biochimica et Biophysica Acta, 1989, vol. 989, pp. 269-280, Elsevier Science Publishers B.V.
Sekar, Vanitha J., et al., "Pharmacokinetic interaction between darunavir boosted with ritonavir and omeprazole or ranitidine in human immunodeficiency virus-negative healthy volunteers," Antimicrobial agents and chemotherapy, Mar. 2007, vol. 51, No. 3, pp. 958-961, American Society for Microbiology.

(Continued)

*Primary Examiner* — Bethany Barham
*Assistant Examiner* — Peter Anthopolos
(74) *Attorney, Agent, or Firm* — Conley Rose, P.C.; Rodney B. Carroll

(57) ABSTRACT

A pharmaceutical composition comprising a solid unit dosage form comprising:
(i) ritonavir or a pharmaceutically acceptable salt and ester thereof;
(ii) darunavir or a pharmaceutically acceptable salt and ester thereof.

14 Claims, No Drawings

(56) References Cited

OTHER PUBLICATIONS

Varmus, Harold, "Retroviruses," Articles, Science, Jun. 10, 1988, vol. 240, pp. 1427-1435.

Weiss, Robin, ed., et al., "Pathogenesis of lentiviruses," RNA Tumor Viruses, 1984, title page, publication page, table of contents, pp. 949-956, Cold Spring Harbor Laboratory.

Foreign communication from a related counterpart application—Japanese First Office Action Translation, JP2010-540173, Jun. 11, 2013, 5 pages.

Chueshov, V. I., et al., "Promyshlennaya tekhnologiya lekarstv (industrial drug technology)," Publisher House UkrFA, 1999, vol. 2, 1 page.

Foreign communication from a related counterpart application—Russian Office Action with translation, RU Application No. 2010131006/15(043925), Mar. 7, 2013, 10 pages.

Foreign communication from a related counterpart application—Russian Office Action with translation, RU Application No. 2010131006/15(043925), Aug. 5, 2013, 10 pages.

L-002022, Date of State Registration is Sep. 22, 2006. Instruction for use: <URL: http://grls.rosminzdrav.ru/Grls_View.aspx?idReg=7754&t=49b06015-32df-40bd-8597-b45d090a092e> and <URL: http://grls.rosminzdrav.ru/InstrImg.aspx?idReg=7754&t=grlsView>, 38 pages.

Madruga, Jose Valdez, et al., "Efficacy and safety of darunavir-ritonavir compared with that of lopinavir-ritonavir at 48 weeks in treatment-experienced, HIV-infected patients in TITAN: a randomised controlled phase III trial," The Lancet, Jul. 7, 2007, vol. 370, 14 pages.

Molina, J. M, et al., "Darunavir (TMC114): a new HIV-1 protease inhibitor," Abstract, 1 page, [Expert Opin Pharmacother, 2007, pp. 1951-1964, vol. 8, No. 12].

Tentsova, A. I., "The dosage form and therapeutic efficacy of drugs (introduction to biopharmacy)," 1974, 2 pages.

Foreign communication from a related counterpart application—English translation of Russian Decision on Grant, Russian Application No. 2010131006/15(043925), Jul. 1, 2014, 6 pages.

\* cited by examiner

ANTI-RETROVIRAL COMBINATION

CROSS-REFERENCE TO RELATED APPLICATIONS

This application is a filing under 35 U.S.C. 371 of International Application No. PCT/GB2008/004291 filed Dec. 24, 2008, entitled "Anti-Retroviral Combination," claiming priority of Indian Patent Application No. 2538/MUM/2007 filed Dec. 24, 2007, which applications are incorporated by reference herein in their entirety.

FIELD OF INVENTION

The present invention relates to a novel antiretroviral combination in particular, to a pharmaceutically stable composition and a process for manufacturing the same thereof.

BACKGROUND OF INVENTION

The human immunodeficiency virus (HIV) is a pathogenic retrovirus and the causative agent of acquired immune deficiency syndrome (AIDS) and related disorders (Barre-Sinossi, F. et al.; 1983, Science 220:868-870; Gallo, R. et al., 1984, Science 224:500-503). There are at least two distinct types of HIV-1 (Barre-Sinossi, F. et al.; 1983, Science 220: 868-870; Gallo, R. et al., 1984, Science 224:500-503) and HIV-2 (Clavel. F. et al., 1986, Science 223:343-346; Guyader, M. et al., 1987, Nature 326:662-669). Further, a large amount of genetic heterogeneity exists within populations of each of these types. Infection of human CD-4+T-lymphocytes with an HIV virus leads to depletion of the cell type and eventually to opportunistic infections, neurological dysfunctions, neoplastic growth, and untimely death.

HIV is a member of the lentivirus family of retroviruses (Teich, N. et al., 1984; RNA Tumor Viruses, Weiss, R. et al., eds., CSH-press, pp. 949-956). Retroviruses are small enveloped viruses that contain a diploid, single-stranded RNA genome, and replicate via a DNA intermediate produced by a virally-encoded reverse transcriptase, an RNA-dependent DNA polymerase (Varmus, H., 1988, Science 240:1427-1439). Other retroviruses include, for example, oncogenic viruses such as human T-cell leukemia viruses (HTLV-1,-II,-III), and feline leukemia virus. The HIV viral particle consists of a viral core, made up of proteins designated p24 and p18. The viral core contains the viral RNA genome and those enzymes required for replicative events. Myristylated gag protein forms an outer viral shell around the viral core, which is, in turn, surrounded by a lipid membrane envelope derived from the infected cell membrane.

The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains noncovalently associated with gp41, possibly in a trimeric or multimeric form (Hammerwskjold, M. and Rekosh, D., 1989, Biochem. Biophys. Acta 989:269-280).

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, Science 228:1094-1096). Thus far, these proteins seem to be the most promising candidates to act as antigens for anti-HIV development. To this end, several groups have begun to use various portions of gp160, gp120, and/or gp41 as immunogenic targets for the host immune systems. See for example, Ivanoff, L. et al., U.S. Pat. No. 5,141,867; Saith, G. et al., WO 92/22,654; Schafferman, A., WO 91/09872; Formoso, C. et al., WO 90/07119. Clinical results concerning these candidate vaccines, however, still remain far in the future.

U.S. Pat. No. 5,541,206 and EP 0674513 B1 discloses the synthesis of Ritonavir.

U.S. Pat. No. 5,541,206 discloses the use of ritonavir to inhibit an HIV infection.

U.S. Pat. No. 5,674,882 discloses the use of ritonavir in combination with one or more HIV protease inhibitors to inhibit an HIV infection.

U.S. Pat. No. 6,037,157 and WO 97/01349 discloses the use of ritonavir to enhance the pharmacokinetics of compounds metabolized by cytochrome P450 monooxygenase.

U.S. Pat. No. 5,484,801 discloses a liquid dosage form of ritonavir for oral administration.

WO 95/07696 discloses an encapsulated solid or semi-solid dosage form for ritonavir.

WO 99/67254 discloses the synthesis of darunavir and the manner in which it may be used to treat HIV infection.

WO 99/67254 discloses the dosage forms suitable for the oral administration of darunavir.

U.S. 2007/0208009 discloses a combination comprising tenofovir, ritonavir and darunavir for treatment or prevention of HIV infections.

None of the current AIDS treatments have proven to be totally effective in treating and/or reversing the disease. In addition, many of the compounds currently used to treat AIDS cause adverse side effects including low platelet count, renal toxicity and bone marrow cytopenia.

Some drugs and, in particular, some HIV protease inhibitors are metabolized by cytochrome P450 monooxygenase, leading to unfavorable pharmacokinetics and hence require more frequent and higher doses, although administration of such drugs with an agent that inhibits metabolism by cytochrome P450 monooxygenase will improve the pharmacokinetics (i.e., increase half-life, increase the time to peak plasma concentration, increase blood levels) of the drug.

Moreover, combination therapy is potentially problematic given the high toxicity of most anti-HIV therapeutics and their low level of effectiveness. Thus, there is a need of a combination therapy which is effective yet non-toxic for treatment-naïve and treatment experienced patients.

Surprisingly, the present inventors have found that a selective combination of darunavir and ritonavir with pharmaceutically acceptable excipients and using simpler manufacturing processes achieves the desired formulation.

We have found that both the actives when admixed per se, show incompatibility and hence there is a need to formulate a stable dosage form.

OBJECT OF THE INVENTION

The object of the present invention is to provide a pharmaceutical composition comprising a novel antiretroviral combination which may be administered simultaneously; separately, or sequentially.

Another object of the present invention is to provide a pharmaceutical composition comprising a novel antiretroviral combination with superior efficacy across the range of treatment-experienced and naïve patients.

Another object of the present invention is to provide a pharmaceutical composition comprising a novel antiretroviral combination which is highly potent against wild-type and multidrug-resistant HIV strains.

Still another object of the present invention is to provide a pharmaceutical antiretroviral composition with ease of manufacture.

It is a further object of the invention to provide a stable composition of darunavir and ritonavir.

SUMMARY OF THE INVENTION

According to one aspect of the present invention, there is provided a pharmaceutical combination comprising:
(i) a protease inhibitor, or a pharmaceutically acceptable salt thereof;
(ii) a cytochrome P450 inhibitor, or a pharmaceutically acceptable salt thereof.

The protease inhibitor is preferably darunavir or a pharmaceutically acceptable salt thereof.

The cytochrome P450 inhibitor is preferably ritonavir or a pharmaceutically acceptable salt thereof.

It will be appreciated that the protease inhibitor, in particular darunavir, may be provided as the free base, or in the form of an appropriate pharmaceutically acceptable salt, a pharmaceutically acceptable solvate, a pharmaceutically acceptable enantiomer, a pharmaceutically acceptable derivative, pharmaceutically acceptable ester, a pharmaceutically acceptable polymorph or a pharmaceutically acceptable prodrug thereof.

It will be appreciated that the cytochrome P450 inhibitor, in particular ritonavir, may be provided as the free base, or in the form of an appropriate pharmaceutically acceptable salt, a pharmaceutically acceptable solvate, a pharmaceutically acceptable enantiomer, a pharmaceutically acceptable derivative, pharmaceutically acceptable ester, a pharmaceutically acceptable polymorph or a pharmaceutically acceptable prodrug thereof.

According to another aspect of the present invention, there is provided an antiretroviral composition comprising one or more protease inhibitors and one or more cytochrome P450 inhibitors, and optionally one or more pharmaceutically acceptable excipients, in a single dose regimen.

According to another aspect of the present invention, there is provided a process of manufacturing the antiretroviral composition comprising one or more protease inhibitors and one or more cytochrome P450 inhibitors.

According to yet another aspect of the present invention, there is provided a pharmaceutical combination comprising one or more protease inhibitors and one or more cytochrome P450 inhibitors, and optionally, one or more pharmaceutically acceptable excipients, for use in treatment against HIV/AIDS.

According to still another aspect of the present invention, there is provided a pharmaceutical combination comprising one or more protease inhibitors and one or more cytochrome P450 inhibitors, and, optionally, one or more pharmaceutically acceptable excipients, for use in the manufacture of a medicament used in the treatment against HIV/AIDS.

Owing to the incompatibility of darunavir and ritonavir, it is a feature of the invention to formulation a composition in which these two active materials are separate from one another.

DETAILED DESCRIPTION OF THE INVENTION

In a preferred embodiment of the present invention, there is provided a composition comprising said combination for inhibition, treatment or prophylaxis of an HIV infection or AIDS (acquired immune deficiency syndrome) in humans by co administering the ritonavir or its pharmaceutically acceptable salts, pharmaceutically acceptable solvates, pharmaceutically acceptable enantiomers, pharmaceutically acceptable derivatives, pharmaceutically acceptable polymorphs, pharmaceutically acceptable ester or pharmaceutically acceptable prodrugs with darunavir or its pharmaceutically acceptable salts, pharmaceutically acceptable solvates, pharmaceutically acceptable enantiomers, pharmaceutically acceptable derivatives, pharmaceutically acceptable polymorphs, pharmaceutically acceptable ester or pharmaceutically acceptable prodrugs.

Preferably, the formulation according to the invention is presented in solid dosage form, conveniently in unit dosage form, and include dosage form suitable for oral, buccal, or vaginal administration.

Solid dosage forms according to the present invention are preferably in the form of tablets, but other conventional dosages such as powders, pellets, capsules and sachets may fall within the scope of the invention.

A preferred formulation according to the invention is in tablet dosage form.

A tablet formulation is the preferred solid dosage form due to its greater stability, less risk of chemical interaction between different medicaments, smaller bulk, accurate dosage, and ease of production.

According to the preferred embodiment, the formulation may be administered simultaneously, separately or sequentially in a single unit dosage form.

According to the preferred embodiment, the combination may be administered by oral, rectal, vaginal routes. For first line therapy of HIV infection, simultaneous administration employing a unitary pharmaceutical formulation is preferred.

For these purposes, the compositions comprising the combination of the present invention, whether co-formulated in a single formulation or formulated for simultaneous, separate or sequential use, may be administered in various dosage forms including tablets, capsules, sachets containing granulated formulation, containing conventional non-toxic pharmaceutically acceptable carriers, adjuvants and vehicles.

Due to formulation problems like incompatibility of the actives, it is difficult to formulate a single layered tablet wherein both the drugs are mixed together. Capsules can be formed by way of granulating both the drugs separately and then filling the capsules.

Hence, the present invention also encompasses a multilayered tablet formulation which can typically be administered to patients and permits or achieves delivery of pharmaceutically active agents effective for the treatment of a specific pathology to be treated, and as such is particularly suited for the treatment of HIV.

According to the preferred embodiment, the formulation may be administered as a multilayer tablet, preferably a bilayer tablet, wherein each layer separately contains a drug and pharmaceutically acceptable excipients which are then compressed to give a bilayer tablet.

According to yet another embodiment, the formulation may be seal coated. According to yet another embodiment, the formulation may be seal coated and further film coated.

According to another preferred embodiment, the present invention also relates to a pharmaceutical composition in a form adapted to be applied to a site where sexual intercourse or related intimate contact can take place, such as the genitals, rectum, mouth, especially the vagina and mouth, comprising a pharmaceutically acceptable carrier and as active ingredients an effective amount of a combination according to the present invention. As appropriate special adapted compositions, there may be cited all compositions usually employed for being applied to the vagina, rectum, mouth such as, for example, vaginal or rectal or buccal tablets.

It will be understood, however, that specific dose level and frequency of dosage of the combination according to the invention for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

According to the preferred embodiment, the combination, according to the invention, will be administered in the following daily dosages; darunavir about 300 to 800 mg, preferably 300 to 600 mg and ritonavir about 50 to 100 mg.

The present invention may be manufactured through various techniques or processes known in the art which includes, but not limited to, direct compression, wet granulation, melt granulation, melt extrusion, spray drying, and solution evaporation.

According to a preferred embodiment, the invention may be processed through hot melt extrusion technique which involves hot melt extrusion of one or more drug(s) with one or more polymer(s), wherein the polymer comprise of one or more water insoluble polymer(s) and/or a combination of one or more water soluble polymer(s) and one or more water insoluble polymer(s) wherein the drug:polymer ratio ranges from 1:1 to 1:6.

In general terms, the process of hot melt extrusion is carried out in the conventional extruders as known to a person skilled in the art.

The melt-extrusion process comprises the steps of preparing a homogeneous melt of one or more drugs, the polymer and the excipients, and cooling the melt until it solidifies. "Melting" means a transition into a liquid or rubbery state in which it is possible for one component to get embedded homogeneously in the other.

Typically, one component will melt and the other components will dissolve in the melt thus forming a solution. Melting usually involves heating above the softening point of the polymer. The preparation of the melt can take place in a variety of ways. The mixing of the components can take place before, during or after the formation of the melt. For example, the components can be mixed first and then melt extruded, or be simultaneously mixed and melt extruded. Usually, the melt is homogenized in order to disperse the active ingredients efficiently. Also, it may be convenient first to melt the polymer and then to mix in and homogenize the active ingredients.

Usually, the melt temperature is in the range from about 50° C. to about 200° C., preferably from about 70° C. to about 200° C., more preferably from about 80° C. to about 180° C., most preferably from about 90° C. to about 150° C.

Suitable extruders include single screw extruders, intermeshing screw extruders or else multiscrew extruders, preferably twin screw extruders, which can be co-rotating or counter-rotating and, optionally, be equipped with kneading disks. It will be appreciated that the working temperatures will also be determined by the kind of extruder or the kind of configuration within the extruder that is used.

The extrudates can be in the form of beads, granulates, tube, strand or cylinder and this can be further processed into any desired shape.

The term "extrudates" as used herein refers to solid product solutions, solid dispersions and glass solutions of one or more drugs with one or more polymers, and optionally pharmaceutically acceptable excipients.

According to a preferred embodiment, a powder blend of the one or more active drug(s) and polymers and optionally pharmaceutical excipients are transferred by a rotating screw of a single screw extruder through the heated barrel of an extruder whereby the powder blend melts and molten solution product is collected on a conveyor where it is allowed to cool to form an extrudate. Shaping of the extrudate can conveniently be carried out by a calender with two counter-rotating rollers with mutually matching depressions on their surface.

A broad range of tablet forms can be attained by using rollers with different forms of depressions. Alternatively, the extrudate is cut into pieces after solidification and can be further processed into suitable dosage forms. More preferably, the extrudates thus finally obtained from the above process are then milled and ground to granules by the means known to a person skilled in the art.

Further, hot melt extrusion is a fast, continuous, single pot manufacturing process without requirement of further drying or discontinuous process steps; it provides short thermal exposure of active allows processing of heat sensitive actives; process temperatures can be reduced by addition of plasticizers; comparatively lower investment for equipment as against other processes. The entire process is anhydrous and the intense mixing and agitation of the powder blend that occur during processing contribute to a very homogenous extrudate(s).

In one aspect, the preferred embodiment in accordance with the present invention may comprise one or more protease inhibitors, or one or more cytochrome P450 inhibitors and one or more water soluble and/or water insoluble polymers which are melt extruded by the process as described herein, where a powder blend of the protease inhibitor, most preferably darunavir, and the cytochrome P450 inhibitor, most preferably ritonavir, and polymer and other optional excipients which may comprise suitable bulking agents and flavourants.

In another aspect, the preferred embodiment in accordance with the present invention may comprise one or more cytochrome P450 inhibitors and one or more water soluble and/or water insoluble polymers which are melt extruded by the process as described herein, where a powder blend of the cytochrome P450 inhibitor, most preferably ritonavir, and polymer and other optional excipients which may comprise suitable bulking agents and flavourants.

The ingredients may be processed to form a powder blend which is transferred through the heated barrel of the extruder, whereby the powder blend melts and molten solution product is collected on a conveyor whereby it is allowed to cool and form an extrudate.

Alternatively, the extrudate may be cut into pieces after solidification and can be further processed into suitable dosage forms. More preferably the extrudates thus finally obtained from the above process are then milled and ground to granules by the means known to a person skilled in the art.

In another aspect, the preferred embodiment in accordance with the present invention may comprise one or more protease inhibitors, or one or more cytochrome P450 inhibitors and a combination of one or more water insoluble polymer and one or more water soluble polymer which are melt extruded by the process as described herein, where a powder blend of the protease inhibitor, most preferably darunavir, and the cytochrome P450 inhibitor, more preferably ritonavir, and a combination of water soluble polymer(s) & water insoluble polymer(s) and other excipients which may comprise suitable bulking agents, plasticizer and flavourants.

The ingredients may be processed to form a powder blend which is transferred through the heated barrel of the extruder, whereby the powder blend melts and molten solution product is collected on a conveyor whereby it is allowed to cool and form an extrudate.

Alternatively, the extrudate may be cut into pieces after solidification and can be further processed into suitable dosage forms. More preferably the extrudates thus finally obtained from the above process are then milled and ground to granules by the means known to a person skilled in the art.

The water soluble polymer may be selected from homopolymers and co-polymers of N-vinyl lactams, especially homopolymers and co-polymers of N-vinyl pyrrolidone e.g., polyvinylpyrrolidone (PVP), co-polymers of PVP and vinyl acetate, co-polymers of N-vinyl pyrrolidone and vinyl acetate or vinyl propionate, cellulose esters and cellulose ethers, high molecular polyalkylene oxides such as polyethylene oxide and polypropylene oxide and co-polymers of ethylene oxide and propylene oxide. It is present in the range wherein the ratio of drug to polymer is 1:1 to 1:6.

The water insoluble polymer may be selected from acrylic copolymers e.g. Eudragit E100 or Eudragit EPO; Eudragit L30D-55, Eudragit FS30D, Eudragit RL30D, Eudragit RS30D, Eudragit NE30D, Acryl-Eze (Colorcon Co.); polyvinylacetate, for example, Kollicoat SR 3OD (BASF Co.); cellulose derivatives such as ethylcellulose, cellulose acetate e.g. Surelease (Colorcon Co.), Aquacoat ECD and Aquacoat CPD (FMC Co.). The water insoluble polymer may be present in the range wherein the ratio of drug to polymer is 1:1 to 1:6.

Plasticizers can be incorporated depending on the polymer and the process requirement. These, advantageously, when used in the hot melt extrusion process decrease the glass transition temperature of the polymer. Plasticizers also help in reducing the viscosity of the polymer melt and thereby allow for lower processing temperature and extruder torque during hot melt extrusion. Examples of plasticizers which can be used in the present invention, include, but are not limited to, polysorbates such as sorbitan monolaurate (Span 20), sorbitan monopalmitate, sorbitan monostearate, sorbitan monoisostearate; citrate ester type plasticizers like triethyl citrate, citrate phthalate; propylene glycol; glycerin; low molecular weight polyethylene glycol; triacetin; dibutyl sebacate, tributyl sebacate; dibutyltartrate, dibutyl phthalate. The plasticizer may be present in an amount ranging from 0% to 10% to the weight of polymer.

According to a preferred embodiment, the present invention may comprise suitable disintegrating agents which includes, but not limited to, croscarmellose sodium, crospovidone, sodium starch glycollate, corn starch, potato starch, maize starch and modified starches, calcium silicates, low substituted hydroxy-propylcellulose. The amount of disintegrating agent is preferably in the range of 5% to 35% by weight of the composition.

According to a preferred embodiment, the present invention may further comprise suitable bulking agents which includes, but are not limited to, saccharides, including monosaccharides, disaccharides, polysaccharides and sugar alcohols such as arabinose, lactose, dextrose, sucrose, fructose, maltose, mannitol, erythritol, sorbitol, xylitol lactitol, and other bulking agents such as powdered cellulose, microcrystalline cellulose, purified sugar, and derivatives thereof. The formulation may incorporate one or more of the above bulking agents, preferably, lactose and microcrystalline cellulose forms the bulking agent. The amount of the bulking agent is preferably in the range of 15% to 70% by weight of the composition.

Accordingly, the present invention may further incorporate suitable lubricants and glidants which may include, but are not limited to, stearic acid and its derivatives or esters like sodium stearate, magnesium stearate and calcium stearate and the corresponding esters such as sodium stearyl fumarate; talc and colloidal silicon dioxide respectively. The amount of lubricant and/or glidant is preferably in the range of 0.25% to 5% by weight of the composition.

According to another embodiment, the present invention may further involve one or more manufacturing process to obtain a single unitary dosage form, i.e., wherein the or each drug is processed by the techniques as discussed above and finally compacted to yield a single dosage form. Preferably, the darunavir and ritonavir in combination with one or more optional excipients is processed with the techniques as discussed above separately and may be combined to form single unitary dosage form. The darunavir blend may be compacted and compressed into a tablet and ritonavir blend may be compacted and compressed into tablet and finally each individual layer may be compressed into a bilayer tablet. More preferably, the tablet may be seal coated. Most preferably, the tablet may be seal coated and finally film coated. The formulation can be coated with Ready colour mix systems (such as Opadry colour mix systems).

According to yet another embodiment, the present invention may be formulated wherein the darunavir is processed through wet granulation, melt granulation, direct compression, melt extrusion and the like as mentioned above and the ritonavir is processed through melt granulation, melt extrusion and the like as mentioned above.

Preferably, the darunavir is mixed with intragranular excipients which includes, but not limited to, diluents, disintegrants and granulated with water, sieved, sifted and lubricated and dried. Alternatively, the dried granules may be compressed into tablets.

Preferably, the ritonavir and one or more excipients which include, but are not limited to, polymers (i.e., either water soluble or water insoluble or mixture thereof), one or more plasticizer, one or more disintegrants, one or more lubricants and glidants are extruded through hot melt extrusion technique wherein extrudates are obtained which can be molded into desired shapes that can be filled in sachets or can be granulated. Alternatively, the granules may be compressed into tablets.

According to a preferred embodiment, the granules (comprising the individual actives) as obtained above may be further mixed, sieved, sifted and filled into capsules or sachets or the granules may be administered directly.

According to yet another embodiment, the or each granules (comprising the individual actives) as obtained above may be individually compressed into two tablets and finally compacted and compressed into a bilayer tablet. Alternatively, the tablet may be seal coated and finally film coated. Alternatively the two tablets can be enclosed in a capsule.

EXAMPLES

The following examples are for the purpose of illustration of the invention only and is not intended in any way to limit the scope of the present invention.

Formula I:

| Sr. No. | Ingredients | Qty/Tab (mg) |
|---|---|---|
| | Drug Premix | |
| 1 | Ritonavir | 100.00 |
| 2 | Colloidal silicon dioxide | 5.00 |
| | Polymer Premix | |
| 3 | Kollidon VA64 | 400.00 |
| 4 | Span 20 | 40.00 |

-continued

| Sr. No. | Ingredients | Qty/Tab (mg) |
|---|---|---|
| | Blending | |
| 5 | Crospovidone | 50.00 |
| 6 | Colloidal silicon dioxide | 5.00 |
| 7 | Microcrystalline cellulose | 50.00 |
| | Lubrication | 5.00 |
| 8 | Sodium stearyl fumarate | 10.00 |
| | Total | 650.00 |
| | Darunavir Layer | |
| 10 | Darunavir | 300.00 |
| 11 | Crospovidone | 10.00 |
| | Binder | |
| 12 | PVP K 30 | 15.00 |
| 13 | Purified water | q.s. |
| | Blending and Lubrication | |
| 14 | Crospovidone | 10.00 |
| 15 | Yellow Iron oxide | 0.50 |
| 16 | Microcrystalline cellulose | 254.00 |
| 17 | Colloidal silicon dioxide | 4.00 |
| 18 | Magnesium stearate | 6.00 |
| | Total | 600.00 |
| | Seal coating | |
| 19 | Opadry AMB OY-B-29000 translucent | 5.00 |
| 20 | Purified water | q.s. |
| | Film coating | |
| 21 | Opadry 04F 52201 Yellow | 15.00 |
| 22 | Purified water | q.s. |
| | Total | 1270 mg |

Process:

(1) Darunavir was mixed with pre-sieved and pre-sifted amounts of crospovidone, yellow iron oxide, polyvinyl pyrrolidone K30, microcrystalline cellulose, colloidal silicon dioxide, magnesium stearate and granulated with purified water.

(2) Ritonavir with small amount of colloidal silicon dioxide was sifted & mixed together with Kollidon VA 64 and Span 20 in a mixer.

(3) The contents obtained in (2) were mixed and finally subjected to hot melt extrusion (HME) wherein the melting temperature for the extrusion process ranges from 70 to 200° C., with the molten mass thus obtained was collected on a conveyor where it was cooled to form extrudates and these extrudates on further milling were converted into granules which was followed by addition of crospovidone, colloidal silicon dioxide and microcrystalline cellulose and further lubricated with sodium stearyl monostearate.

(4) The granules obtained in (1) and (3) were compressed together to form a bilayer tablet which was then seal coated and finally film coated.

Formula II:

| Sr. No. | Ingredients | Qty (mg/tab) |
|---|---|---|
| | Darunavir Part | |
| | Dry mix | |
| 1. | Darunavir Ethanolate | 325.00 |
| 2. | Microcrystalline cellulose | 145.00 |
| 3. | Crospovidone | 10.0 |

-continued

| Sr. No. | Ingredients | Qty (mg/tab) |
|---|---|---|
| | Binder | |
| 4. | Povidone (PVP K-30) | 15.00 |
| 5. | Purified Water | q.s. |
| | Extragranular | |
| 6. | Microcrystalline cellulose | 110.00 |
| 7. | Crospovidone | 10.00 |
| | Lubrication | |
| 8. | Colloidal silicon dioxide | 4.00 |
| 9. | Magnesium stearate | 6.00 |
| | Total | 625.0 |
| | Ritonavir Part | |
| | Active Part | |
| 10 | Ritonavir | 50.00 |
| 11 | Colloidal silicon Dioxide (Aerosil 200) | 3.45 |
| | Polymer Part | |
| 12. | Kollidon VA 64 | 246.50 |
| 13. | Polyoxyl 40 hydrogenated castor oil | 33.35 |
| | Blending & Lubrication | |
| 14. | Colloidal silicon Dioxide (Aerosil 200) | 6.95 |
| 15. | Dibasic Calcium Phosphate (Anhydrous) | 84.70 |
| | Total | 1050.00 |
| | Film coating | |
| 16 | Opadry II 85G82999 Yellow | 25.00 |
| 17 | Purified Water | q.s. |
| | Total | 1075.00 |

Process:

(1) Darunavir Ethanolate was mixed with pre-sieved and presifted quantities of crospovidone and microcrystalline cellulose and granulated with PVP K-30 followed by mixing and lubrication with crospovidone, microcrystalline cellulose, colloidal silicon dioxide and magnesium stearate.

(2) Ritonavir with small amount of colloidal silicon dioxide was sifted and mixed together with Kollidon VA 64 and polyoxyl 40 hydrogenated castor oil in a mixer.

(3) The contents obtained in (2) were mixed and finally subjected to hot melt extrusion (HME) wherein the melting temperature for the extrusion process ranges from 70 to 200° C., with the molten mass thus obtained was collected on a conveyor where it was cooled to form extrudates and these extrudates on further milling were converted into granules which was followed by addition of colloidal silicon dioxide and anhydrous dibasic calcium phosphate.

(4) The granules obtained in (1) and (3) were compressed together to form a bilayer tablet which was then finally film coated.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "a polymer" includes a single polymer as well as two or more different polymers; reference to a "plasticizer" refers to a single plasticizer or to combinations of two or more plasticizer, and the like.

The invention claimed is:

1. A pharmaceutical compositon comprising a tablet dosage form comprising:
    a first layer comprising ritonavir in an amount of 50 mg, collidal silicon dioxide, vinylpyrrolidone-vinyl acetate copolymer, polyoxl 40 hydrogenated castor oil, and dibasic calcium phosphate, and wherein the first layer is absent of darunavir ethanolate; and
    a second layer comprising the darunavir ethanolate in an amount of 325 mg, microcrystalline cellulose, crospovidone, povidone, collidal silicon dioxide, and magnesium stearate, and wherein the second layer is absent of the ritonavir.

2. The pharmaceutical composition according to claim 1, wherein the ritonavir of the first layer is present in granules obtained via hot melt extrusion with the collidal silicon dioxide, the vinylpyrrolidone-vinyl acetate copolymer, and the poloxyl 40 hydrogenated castor oil.

3. The pharmaceutical composition according to claim 2, wherein a melting temperature for the hot melt extrusion ranges from 70° to 200° C.

4. The pharmaceutical composition according to claim 1, wherein a ratio of the weight of the ritonavir to the weight of the vinylpyrrolidone-vinyl acetate copolymer is from 1:1 to 1:6.

5. The pharmaceutical composition according to claim 1, wherein the darunavir ethanolate of the second layer is present in granules obtained via wet granulation with povidone.

6. A method of treating HIV or AIDS comprising administering a therapeutically effective amount of the pharmaceutical composition as defined in claim 1.

7. The pharmaceutical composition according to claim 1, wherein the tablet dosage form has a film coating.

8. A pharmaceutical composition comprising a tablet dosage form comprising:
    a first layer comprising ritonavir in an amount of 100 mg, colloidal silicon dioxide, yinylpyrrolidone-vinyl acetate copolymer, sorbitan monolaurate, crospovidone, microcrystalline cellulose, and sodium stearyl monostearate, and wherein the first layer is absent of darunavir; and
    a second layer comprising the danmavir in an amount of 300 mg, crospovidone, povidone, yellow iron oxide, microcrystalline cellulose, colloidal silicon dioxide, and magnesium stearate, and wherein the second layer is absent of the ritonavir.

9. The pharmaceutical composition according to claim 8, wherein the ritonavir of the first layer is present in granules obtained via hot melt extrusion with the colloidal silicon dioxide, the yinylpyrrolidone-vinyl acetate copolymer, and sorbitan monolaurate.

10. The pharmaceutical composition according to claim 9, wherein a melting temperature for the hot melt, extrusion ranges from 70° C. to 200° C.

11. The pharmaceutical composition according to claim 8, wherein the darunavir of the second layer is present in granules obtained via wet granulation with purified water.

12. The pharmaceutical composition according to claim 8, wherein a ratio of the weight of the ritonavir to the weight of the vinylpyrrolidone-vinyl acetate copolymer is from 1:1 to 1:6.

13. The pharmaceutical composition according to claim 8, wherein the tablet dosage form has a film coating.

14. A method of treating HIV or AIDS comprising administering a therapeutically effective amount of the pharmaceutical composition as defined in claim 8.

* * * * *

UNITED STATES PATENT AND TRADEMARK OFFICE
CERTIFICATE OF CORRECTION

| | | |
|---|---|---|
| PATENT NO. | : 9,339,470 B2 | Page 1 of 1 |
| APPLICATION NO. | : 12/810301 | |
| DATED | : May 17, 2016 | |
| INVENTOR(S) | : Amar Lulla and Geena Malhotra | |

It is certified that error appears in the above-identified patent and that said Letters Patent is hereby corrected as shown below:

In the claims:

Claim 1, column 11, line 15, replace "collidal" with --colloidal--.

Claim 1, column 11, line 16, replace "polyoxl" with --polyoxyl--.

Claim 1, column 11, line 21, replace "collidal" with --colloidal--.

Claim 2, column 11, line 26, replace "collidal" with --colloidal--.

Claim 2, column 11, line 28, replace "poloxyl" with --polyoxyl--.

Claim 3, column 11, line 31, replace "from 70° to 200° C." with --from 70° C. to 200° C.--.

Claim 8, column 12, line 9, replace "yinylpyrrolidone-vinyl" with --vinylpyrrolidone-vinyl--.

Claim 8, column 12, line 13, replace "danmavir" with --darunavir--.

Claim 9, column 12, line 22, replace "yinylpyrrolidone-vinyl" with --vinylpyrrolidone-vinyl--.

Claim 10, column 12, line 25, replace "hot melt, extrusion" with --hot melt extrusion--.

Signed and Sealed this
Ninth Day of August, 2016

Michelle K. Lee
*Director of the United States Patent and Trademark Office*